(12) United States Patent
Amino

(10) Patent No.: US 8,394,970 B2
(45) Date of Patent: Mar. 12, 2013

(54) PROCESS FOR MANUFACTURING A GLUTAMIC ACID DERIVATIVE AND A PYROGLUTAMIC ACID DERIVATIVE AND A NOVEL INTERMEDIATE IN THE MANUFACTURE THEREOF

(75) Inventor: Yusuke Amino, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 553 days.

(21) Appl. No.: 12/500,135

(22) Filed: Jul. 9, 2009

(65) Prior Publication Data

US 2010/0010234 A1 Jan. 14, 2010

Related U.S. Application Data

(60) Division of application No. 11/169,677, filed on Jun. 30, 2005, now Pat. No. 7,674,915, which is a continuation of application No. PCT/JP03/17016, filed on Dec. 26, 2003.

(30) Foreign Application Priority Data

Jan. 9, 2003 (JP) ................................. 2003/003626

(51) Int. Cl.
*C07D 209/00* (2006.01)
*C07D 209/04* (2006.01)
(52) U.S. Cl. ........................................ 548/492; 548/494
(58) Field of Classification Search .................. None
See application file for complete search history.

(56) References Cited

U.S. PATENT DOCUMENTS

| | | | |
|---|---|---|---|
| 5,106,962 | A | 4/1992 | Amino et al. |
| 5,128,164 | A | 7/1992 | Van Wyk et al. |
| 5,128,482 | A | 7/1992 | Olivier et al. |
| 5,994,559 | A | 11/1999 | Abushanab et al. |
| 6,794,531 | B2 | 9/2004 | Nagashima et al. |
| 6,939,987 | B2 | 9/2005 | Amino et al. |
| 7,329,427 | B2 | 2/2008 | Amino et al. |
| 7,390,909 | B2 | 6/2008 | Kawahara et al. |
| 2006/0009394 | A1 | 1/2006 | Amino | |

FOREIGN PATENT DOCUMENTS

| | | |
|---|---|---|
| JP | 64-25757 | 1/1989 |
| JP | 4-217954 | 8/1992 |
| JP | 2002-0603282 A | 2/2002 |
| ZA | 87/4288 | 6/1987 |

OTHER PUBLICATIONS

Xian-Man Zhang et al., J. Org. Chem., vol. 58, pp. 3060-3066 (1993).
Frederick G. Bordwell et al., J. Org. Chem., vol. 46, pp. 4327-4331 (1981).
Frederick G. Bordwell et al., J. Org. Chem. vol. 56, pp. 4218-4223 (1991).
D. Oliviera and F. Coelho. Synthetic Communications. (2000) 30(12), pp. 2143-2159.
Pedro Merino et al, "1,3-Dipolar Cycloaddition of Furfury Nitrones with Acrylates, A Convenient Approach to Protected 4-Hydroxypyrogiutamic Acids", *Journal of Organic Chemistry*, Mar. 10, 2000. vol. 65, No. 5, pp. 1590-1596.
R. Vleggaar et al, "Structure Elucidation of Monatin, a High-intensity Sweetener Isolated from the Plant *Schlerochiton ilicifolius*", *J. Chem. Soc. Perkin Trans.* 1, 1992, pp. 3095-3098.
C. W. Holzapfel et al, "A Simple Cycloaddition Approach to a Racemate of the Natural Sweetener Monatin", *Synthetic Communications*, 1994, vol. 24, No. 22, pp. 3197-3211.
K. Nakamura et al, "Total Synthesis of Monatin", *Organic Letters*, 2000, vol. 2, No. 19, pp. 2967-2970.
D. J. Oliveira et al, "Diastereoselective formation of a quaternary center in a pyroglutamate derivative. Formal synthesis of Monatin", *Tetrahedron Letters*, 2001, vol. 42, pp. 6793-6796.
J. Ezquerra et al, "Stereoselective Double Alkylation of Ethyl *N*-Boc-pyroglutamate", *J. Org. Chem.*, 1994, vol. 59, No. 15, pp. 4327-4331.
X. Zhang et al, "A convenient and high yield method to prepare 4-hydroxypyroglutamic acids", *Tetrahedron Letters*, 2001, vol. 42, pp. 5335-5338.
T. W. Greene et al, *Protection Groups in Organic Synthesis*, Third Edition, John Wiley & Sons, Inc., 1999, pp. 127-132, 383-387 and 642-643.
P. O. Larsen et al, "2(*S*),4(*R*)-4-(β-D-Galactopyranosyloxy)4-Isobutyl-Glutamic Acid: A New Amino Acid in *Reseda odorata*", *Phvtochemistry*, 1973, vol. 12, pp. 1713-1719.
L.J. Heinz et al., "An Efficient Synthesis of cis- and trans-Methyl-3-hydroxy-2-pyrrolidone-5-carboxylates, Key Intermediates for the Synthesis of γ-Substituted Glutamic Acid Analogs", J. Organic Chem. 1996, 61, 4838-4841.
Interference Appl. No. 105,696, filed Jun. 25, 2009, Kawahara et al.
Office Action dated Feb. 3, 2010, in European Patent Application No. 03815609.7.
Office Action dated Nov. 11, 2010, in Korean Patent Application No. 10-2005-7012825.
K. Nakamura et al., Organic Letters, vol. 2, No. 19, pp. 2967-2970 (2000).
Office Action issued May 11, 2010, in Japanese Patent Application No. 2004-567573 (with English translation).
Office Action issued Jul. 28, 2011, in Korean Patent Application No. 10-2005-7012825.

*Primary Examiner* — Julie Ha
(74) *Attorney, Agent, or Firm* — Oblon, Spivak, McClelland, Maier & Neustadt, L.L.P.

(57) ABSTRACT

Glutamic acid derivatives, in particular monatin, may be conveniently prepared by alkylating a 4-protected hydroxyl pyroglutamic acid derivative with an alkylating agent to prepare a 4-protected hydroxyl-4-alkylglutamic acid derivative, followed by the steps of hydrolysis and deprotection. The 4-protected hydroxyl pyroglutamic acid derivative is easy to produce from hydroxyproline. The 4-protected hydroxyl pyroglutamic acid derivative is particularly suitable for use in the efficient manufacture of monatin of high optical purity, since it can be alkylated selectively at the 4-position and stereoselectively and after its alkylation, it can easily be converted to a glutamic acid derivative.

7 Claims, No Drawings

PROCESS FOR MANUFACTURING A GLUTAMIC ACID DERIVATIVE AND A PYROGLUTAMIC ACID DERIVATIVE AND A NOVEL INTERMEDIATE IN THE MANUFACTURE THEREOF

CROSS REFERENCES TO RELATED APPLICATIONS

This application is a division of U.S. patent application Ser. No. 11/169,677, filed on Jun. 30, 2005, now U.S. Pat. No. 7,674,915 which is a continuation of International Patent Application No. PCT/JP03/017016, filed on Dec. 26, 2003, and claims priority to Japanese Patent Application No. 003626/2003, filed on Jan. 9, 2003, both of which are incorporated herein by reference in their entireties.

BACKGROUND OF THE INVENTION

1. Field of the Invention

The present invention relates to processes for manufacturing glutamic acid derivatives and pyroglutamic acid derivatives, in particular monatin, and novel intermediates used in the manufacture thereof by that process.

2. Discussion of the Background

Specific glutamic acid derivatives, including monatin as a typical example, are compounds expected to be useful as sweeteners, or intermediates in the manufacture of drugs, etc. Monatin is a naturally occurring amino acid derivative isolated from the bark of the root of *Schlerochiton ilicifolius*, a plant growing naturally in the northern Transvaal area of South Africa and its structure has been reported by R. Vleggaar et al as being of (2S,4S)-2-amino-4-carboxy-4-hydroxy-5-(3-indolyl) pentanoic acid ((2S,4S)-4-hydroxy-4-(3-indolyl-methyl)-glutamic acid; see formula (19) below) (see R. Vleggaar et al, *J. Chem. Soc. Perkin Trans.*, pp. 3095-3098 (1992)).

The same literature reports that the (2S, 4S) form of monatin reportedly obtainable from a natural plant has a sweetness (or sweetness intensity) which is 800 or 1,400 times that of sucrose. Several methods have been reported as methods of synthesizing monatin, but to date there has not been any industrially suitable method (for examples of synthesis, reference is made to Republic of South Africa Patent Application No. 87/4288 (P. J. van Wyk et al, ZA87/4288); C. W. Holzapfel et al, *Synthetic Communications*, vol. 24(22), pp. 3197-3211 (1994); U.S. Pat. No. 5,994,559; and K. Nakamura et al, *Organic Letters*, vol. 2, pp. 2967-2970 (2000), etc.).

D. J. Oliveira et al (see, *Tetrahedron Letters*, vol. 42, pp. 6793-6796 (2001)) have reported that a monatin derivative having a protective group as shown by formula (17) below can be synthesized stereoselectively by alkylating a lactam derivative as shown by formula (16) below and subjecting it to hydrolysis and an oxidizing reaction.

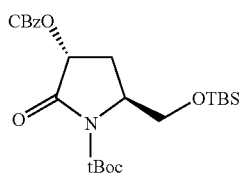

(16)

(where TBDMS stands for a t-butyldimethylsilyl group, Cbz stands for a benzyloxycarbonyl group, tBoc stands for a t-butoxycarbonyl group and Et stands for an ethyl group.)

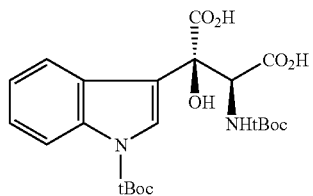

(17)

(where tBoc is as defined above.)

However, this method involves complicated procedures including reducing the carboxyl group of a pyroglutamic acid derivative into a hydroxymethyl group, converting it to a protected hydroxymethyl group and introducing a hydroxyl group into the 4-position for the preparation of compound (16), and after the alkylation of compound (16), conducting the deprotection of the protected hydroxymethyl group into a hydroxymethyl group and oxidizing it back into a carboxyl group, though the compound represented by formula (16) is capable of regioselective alkylation as it has only a single active hydrogen atom.

Chromium trioxide ($CrO_3$) is used in the oxidizing reaction, but the reaction using it presents a great many problems as a method of manufacture, since this reagent is dangerous because of toxicity, etc. Moreover, it is not desirable for any process of manufacture to include any oxidizing reaction of any compound having an indole ring, since the indole ring is easily oxidizable.

As regards the alkylation at the 4-position of a pyroglutamic acid derivative having a carboxyl group which is not reduced, which differs from the above case, J. Ezquerra et al (see, *J. Org. Chem.*, vol. 59, pp. 4327-4331 (1994)) have, for example, reported a method of producing a 4,4-dialkylpyroglutamic acid derivative by dialkylating the 4-position of a pyroglutamic acid derivative represented by formula (18) below.

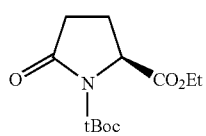

(18)

(where tBoc and Et are as defined above.)

However, there has not been reported any case of the selective alkylation at the 4-position of a pyroglutamic acid derivative having a protected hydroxyl group at the 4-position and having a carboxyl group which is reduced like a compound represented by formula (1) below.

Thus, there remains a need for processes for manufacturing glutamic acid derivatives and pyroglutamic acid derivatives, in particular monatin, and novel intermediates used in the manufacture thereof by that process.

SUMMARY OF THE INVENTION

Accordingly, it is one object of the present invention to provide novel methods for the manufacture of glutamic acid derivatives.

It is another object of the present invention to provide novel methods for the efficient and easy manufacture of glutamic acid derivatives.

It is another object of the present invention to provide novel methods for the manufacture of monatin.

It is another object of the present invention to provide novel methods for the efficient and easy manufacture of monatin.

It is another object of the present invention to provide novel compounds which are useful as intermediates in the manufacture of glutamic acid derivatives, in particular monatin, and which are suitable for industrial production These and other objects, which will become apparent during the following detailed description, have been achieved by the inventor's study of 4-protected hydroxy-pyroglutamic acid derivatives having a protected hydroxyl group at the 4-position and not having a carboxyl group which is reduced, as represented by formula (1), and the finding that when the derivative is subjected to an alkylation reaction, its regio- and stereo-selective alkylation at the 4-position is possible.

Although two sites, i.e., the 2- and 4-positions, have been considered as the reaction sites for alkylation performed by causing an alkylating agent to react with a 4-protected hydroxypyroglutamic acid derivative as represented by formula (1), the inventor has found from their study that it is possible to alkylate selectively the 4-position of the 4-protected hydroxyl-pyroglutamic acid derivative. The inventor has also found that the alkylation at the 4-position of the 4-protected hydroxypyroglutamic acid derivative proceeds stereoselectively. More specifically, its alkylation at the 4-position proceeds from the side of the pyrrolidone ring opposite from the substituent (—$CO_2R^1$) at the 2-position. Accordingly, the relative configuration at the 2- and 4-positions of a 4-protected hydroxy-4-substituted pyroglutamic acid derivative as obtained by an alkylation reaction coincides with the relative configuration at the 2- and 4-positions of (2S, 4S) or (2R, 4R)-monatin among four kinds of stereoisomers of monatin and it is possible to derive monatin having the corresponding configuration.

The inventor has also found that the 4-protected hydroxy-4-substituted pyroglutamic acid derivative obtained by an alkylation reaction makes it possible to manufacture easily a glutamic acid derivative, typically monatin, simply by the lactam hydrolysis and deprotection of the protecting group.

The present invention is based on our findings. Thus, the present invention provides:

(1) A method of manufacturing a glutamic acid compound represented by formula (3) below (including one in the form of a salt), comprising:

(a) subjecting a 4-protected hydroxy-pyroglutamic acid compound represented by formula (1) below (including one in the form of a salt) to an alkylation reaction to obtain a 4-protected hydroxy-4-substituted pyroglutamic acid compound represented by formula (2) below (including one in the form of a salt); and (b) subjecting the compound represented by formula (2) below (including one in the form of a salt) to hydrolysis and deprotection:

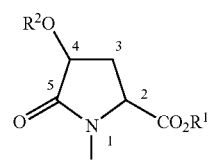

(1)

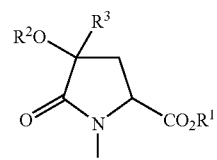

(2)

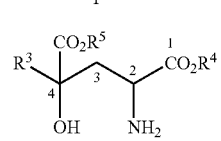

(3)

where $R^1$, $R^4$ and $R^5$ each independently of one another represent a group selected from a hydrogen atom and a hydrocarbon group, $R^2$ represents a protecting group for a hydroxyl group, $R^3$ represents a group selected from a hydrocarbon group optionally having a substituent and a heterocyclyl hydrocarbon group optionally having a substituent, and P stands for a protecting group for an imino group.

(2) A method of manufacturing a 4-protected hydroxy-4-substituted pyroglutamic acid compound represented by formula (2) below (including one in the form of a salt), comprising:

(a) subjecting a 4-protected hydroxypyroglutamic acid compound represented by formula (1) below (including one in the form of a salt) to an alkylation reaction:

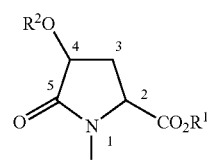

(1)

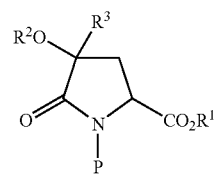

(2)

where $R^1$ represents a group selected from a hydrogen atom and a hydrocarbon group, $R^2$ represents a protecting group for a hydroxyl group, $R^3$ represents a group selected from a hydrocarbon group optionally having a substituent and a heterocyclyl hydrocarbon group, and P stands for a protecting group for an imino group.

(3) A method of manufacturing a glutamic acid compound represented by formula (3) below (including one in the form of a salt), comprising:

(a) subjecting a 4-protected hydroxy-4-substituted pyroglutamic acid compound represented by formula (2) below (including one in the form of a salt) to hydrolysis and deprotection:

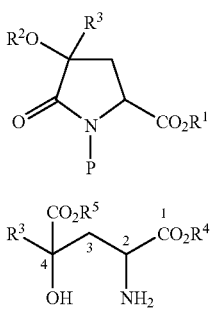

where $R^1$, $R^4$ and $R^5$ each independently of one another represent a group selected from a hydrogen atom and a hydrocarbon group, $R^2$ stands for a protecting group for a hydroxyl group, $R^3$ stands for a group selected from a hydrocarbon group optionally having a substituent and a heterocyclyl hydrocarbon group optionally having a substituent, and P stands for a protecting group for an imino group.

(4) A method as set forth in (1) or (3) above, wherein $R^1$ represents a group selected from an alkyl group having 1 to 5 carbon atoms and a benzyl group, $R^4$ and $R^5$ each represents a hydrogen atom, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, $R^3$ represents a group selected from an alkyl group having 1 to 20 carbon atoms, an aryl group having 1 to 20 carbon atoms, an aralkyl group having 1 to 20 carbon atoms, and a heterocyclyl hydrocarbon group having 1 to 20 carbon atoms, and P stands for a group selected from the group consisting of a t-butoxycarbonyl group, a benzyloxycarbonyl group, and a benzyl group.

(5) A method as set forth in (2) above, wherein $R^1$ represents a group selected from an alkyl group having 1 to 5 carbon atoms and a benzyl group, $R^2$ represents a group selected from a t-butyldimethylsilyl group, a trimethylsilyl group, a t-butyldiphenylsilyl group, a benzyl group, a t-butyl group, a benzyloxycarbonyl group, and a t-butoxycarbonyl group, $R^3$ represents a group selected from an alkyl group having 1 to 20 carbon atoms, an aryl group having 1 to 20 carbon atoms, an aralkyl group having 1 to 20 carbon atoms, and a heterocyclyl hydrocarbon group having 1 to 20 carbon atoms, and P represents a group selected from a t-butoxycarbonyl group, a benzyloxycarbonyl group, and a benzyl group.

(6) A method as set forth in any of (1) to (3) above, wherein $R^3$ is a benzyl group or an N-protected-3-indolylmethyl group.

(7) A method as set forth in (1) or (2) above, wherein the alkylation reaction is performed in the presence of an alkylating agent represented by formula (4) below:

$$R^3-X \qquad (4)$$

where $R^3$ represents a group selected from the group consisting of a hydrocarbon group optionally having a substituent and a heterocyclyl hydrocarbon group optionally having a substituent, and X represents a halogen atom.

(8) A method as set forth in (7) above, wherein the alkylation reaction is performed in the presence of a base.

(9) A method as set forth in (7) above, wherein the base is one or more kinds of base selected from the group consisting of a lithium salt of hexamethyldisilazane, lithium hexamethyldisilazanide, a potassium salt of hexamethyldisilazane, potassium hexamethyl-disilazanide, a sodium salt of hexamethyldisilazane, sodium hexamethyldisilazanide, lithium diisopropylamide, and normal-butyl lithium.

(10) A method as set forth in (7) above, wherein the base is used in a molar ratio of between 1.0 and 2.0 to 1 relative to the 4-protected hydroxyglutamic acid compound.

(11) A method of manufacturing a monatin compound represented by formula (7) below (including one in the form of a salt), comprising:

(a) reacting a 4-protected hydroxy-pyroglutamic acid compound represented by formula (1) below (including one in the form of a salt) with N-protected-3-halogenomethylindole represented by formula (5) below to obtain a 4-protected hydroxy-4-substituted pyroglutamic acid compound represented by formula (6) below (including one in the form of a salt); and (b) subjecting the 4-protected hydroxy-4-substituted pyroglutamic acid compound represented by formula (6) to hydrolysis and deprotection:

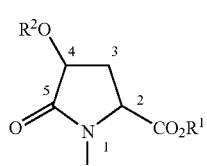

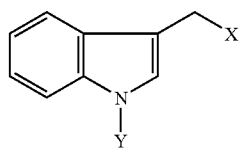

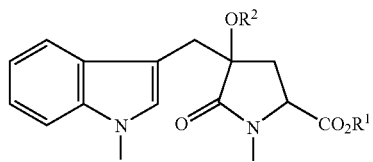

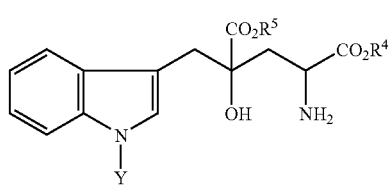

where $R^1$, $R^4$ and $R^5$ each independently of one another represent a group selected from a hydrogen atom and a hydrocarbon group, $R^2$ represents a protecting group for a hydroxyl group, X represents a halogen atom, P represents a protecting group for an imino group, and Y represents a protecting group for an indolyl group.

(12) A method of manufacturing a 4-protected hydroxy-4-substituted pyroglutamic acid compound represented by formula (6) below (including one in the form of a salt), comprising:

(a) reacting a 4-protected hydroxypyroglutamic acid compound represented by formula (1) below (including one in the form of a salt) with N-protected-3-halogeno-methylindole represented by formula (5) below:

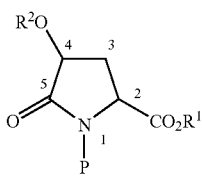
(1)

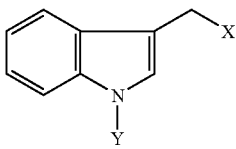
(5)

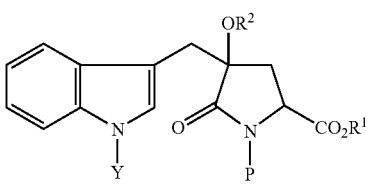
(6)

where R¹ represents a group selected from a hydrogen atom and a hydrocarbon group, R² represents a protecting group for a hydroxyl group, X represents a halogen atom, P represents a protecting group for an imino group, and Y represents a protecting group for an indolyl group.

(13) A method of manufacturing a monatin compound represented by formula (7) below (including one in the form of a salt), comprising:

(a) subjecting a 4-protected hydroxy-4-substituted pyroglutamic acid compound represented by formula (6) below (including one in the form of a salt) to hydrolysis and deprotection:

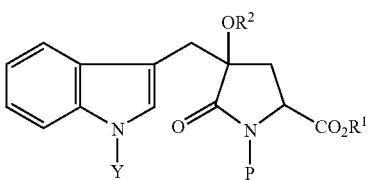
(6)

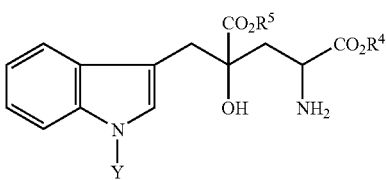
(7)

where $R^1$, $R^4$ and $R^5$ each independently of one another represent a group selected from a hydrogen atom and a hydrocarbon group, $R^2$ represents a protecting group for a hydroxyl group, P represents a protecting group for an imino group, and Y represents a protecting group for an indolyl group.

(14) A method as set forth in (11) above, wherein $R^{11}$ represents a group selected from an alkyl group having 1 to 5 carbon atoms and a benzyl group, $R^4$ and $R^5$ represent a hydrogen atom each, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, X represents a group selected from the group consisting of a chlorine atom, a bromine atom, and an iodine atom, and P and Y each independently of each other represent a group selected from the group consisting of a t-butoxycarbonyl group, a benzyloxycarbonyl group, and a benzyl group.

(15) A method as set forth in (12) above, wherein $R^1$ represents a group selected from the group consisting of a hydrogen atom, an alkyl group having 1 to 5 carbon atoms, and a benzyl group, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, X represents a group selected from the group consisting of a chlorine atom, a bromine atom, and an iodine atom, and P and Y each independently of each other represent a group selected from the group consisting of a t-butoxycarbonyl group, a benzyloxycarbonyl group, and a benzyl group.

(16) A method as set forth in (13) above, wherein $R^1$ represents a group selected from an alkyl group having 1 to 5 carbon atoms and a benzyl group, $R^4$ and $R^5$ each represent a hydrogen atom, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, and P and Y each independently of each other represent a group selected from the group consisting of a t-butoxycarbonyl group, a benzyloxycarbonyl group, and a benzyl group.

(17) A method as set forth in (11) or (12) above, wherein the alkylation reaction is performed in the presence of a base.

(18) A method as set forth in (17) above, wherein the base is one or more kinds of base selected from the group consisting of a lithium salt of hexamethyldisilazane, lithium hexamethyldisilazane, a potassium salt of hexamethyldisilazane, potassium hexamethyl-disilazane, a sodium salt of hexamethyldisilazane, sodium hexamethyldisilazane, lithium diisopropylamide, and normal butyl lithium.

(19) A method as set forth in (17) above, wherein the base is used in a molar ratio of between 1.0 and 2.0 to 1 relative to the 4-protected hydroxyglutamic acid compound.

(20) A method of manufacturing an optically active monatin compound represented by formula (10) below (including one in the form of a salt), comprising:

(a) reacting an optically active 4-protected hydroxy-pyroglutamic acid compound represented by formula (8) below (including one in the form of a salt) with N-protected-3-halogenomethylindole represented by formula (5) below to obtain an optically active 4-protected hydroxy-4-substituted pyroglutamic acid compound represented by formula (9) below (including one in the form of a salt); and (b) subjecting the optically active 4-protected hydroxy-4-substituted pyroglutamic acid compound represented by formula (9) to hydrolysis and deprotection:

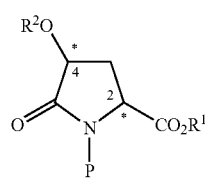
(8)

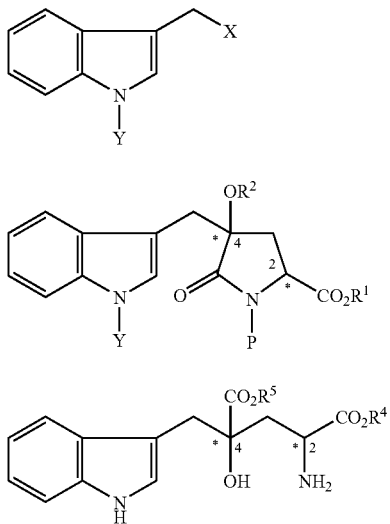

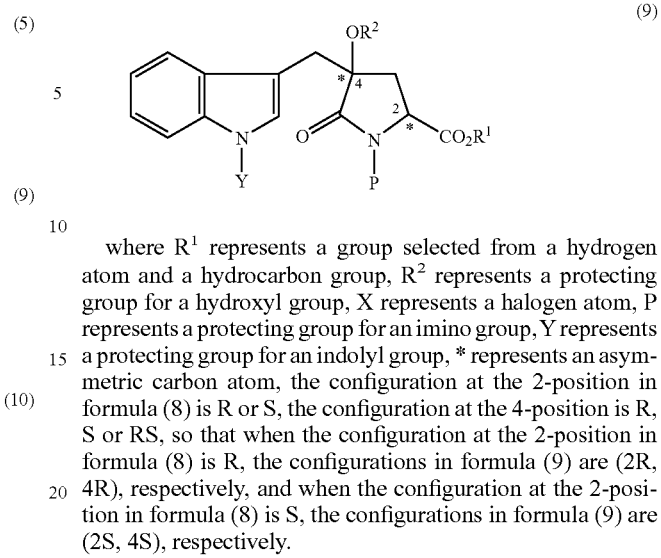

where $R^1$ represents a group selected from a hydrogen atom and a hydrocarbon group, $R^2$ represents a protecting group for a hydroxyl group, X represents a halogen atom, P represents a protecting group for an imino group, Y represents a protecting group for an indolyl group, * represents an asymmetric carbon atom, the configuration at the 2-position in formula (8) is R or S, the configuration at the 4-position is R, S or RS, so that when the configuration at the 2-position in formula (8) is R, the configurations in formula (9) are (2R, 4R), respectively, and when the configuration at the 2-position in formula (8) is S, the configurations in formula (9) are (2S, 4S), respectively.

(22) A method of manufacturing an optically active monatin compound represented by formula (10) below (including one in the form of a salt), comprising:

(a) subjecting an optically active 4-protected hydroxy-4-substituted pyroglutamic acid compound represented by formula (9) below (including one in the form of a salt) to hydrolysis and deprotection:

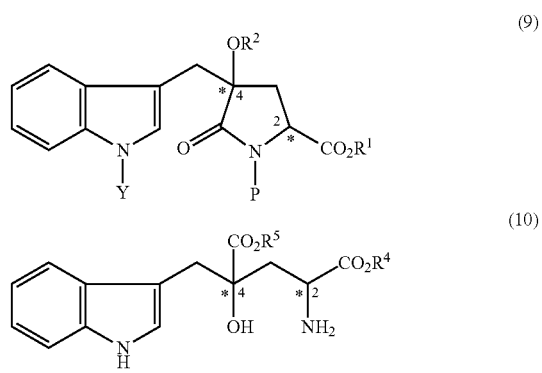

where $R^1$, $R^4$ and $R^5$ each independently of one another represent a group selected from a hydrogen atom and a hydrocarbon group, $R^2$ represents a protecting group for a hydroxyl group, P represents a protecting group for an imino group, Y represents a protecting group for an indolyl group, * represents an asymmetric carbon atom, and when the configuration in formula (9) is (2R, 4R), the configuration in formula (10) is (2R, 4R), and when the configuration in formula (9) is (2S, 4S), the configuration in formula (10) is (2S, 4S).

(23) A method as set forth in (20) above, wherein $R^1$ represents a group selected from an alkyl group having 1 to 5 carbon atoms and a benzyl group, $R^4$ and $R^5$ each represent a hydrogen atom, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, X represents a group selected from the group consisting of a chlorine atom, a bromine atom, and an iodine atom, and P and Y each independently of each other represent a group selected from the group consisting of a t-butoxycarbonyl group, a benzyloxycarbonyl group and a benzyl group.

where $R^1$, $R^4$ and $R^5$ each independently of one another represent a group selected from a hydrogen atom and a hydrocarbon group, $R^2$ represents a protecting group for a hydroxyl group, X represents a halogen atom, P represents a protecting group for an imino group, Y represents a protecting group for an indolyl group, * represents an asymmetric carbon atom, the configuration at the 2-position in formula (8) is R or S, the configuration at the 4-position is R, S or RS, so that when the configuration at the 2-position in formula (8) is R, the configurations in formulas (9) and (10) are (2R, 4R), respectively, and when the configuration at the 2-position in formula (8) is S, the configurations in formulas (9) and (10) are (2S, 4S), respectively.

(21) A method of manufacturing an optically active 4-protected hydroxy-4-substituted pyroglutamic acid compound represented by formula (9) below (including one in the form of a salt), comprising:

(a) reacting an optically active 4-protected hydroxy-pyroglutamic acid compound represented by formula (8) below (including one in the form of a salt) with N-protected-3-halogenomethylindole represented by formula (5) below:

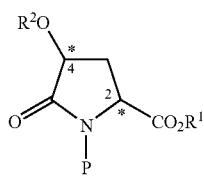

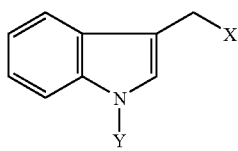

(24) A method as set forth in (21) above, wherein $R^1$ represents a group selected from the group consisting of a hydrogen atom, an alkyl group having 1 to 5 carbon atoms, and a benzyl group, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, X represents a group selected from the group consisting of a chlorine atom, a bromine atom, and an iodine atom, and P and Y each independently of each other represent a group selected from the group consisting of a t-butoxycarbonyl group, a benzyloxycarbonyl group, and a benzyl group.

(25) A method as set forth in (22) above, wherein $R^1$ represents a group selected from an alkyl group having 1 to 5 carbon atoms and a benzyl group, $R^4$ and $R^5$ each represent a hydrogen atom, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, and P and Y each independently of each other represent a group selected from the group consisting of a t-butoxycarbonyl group, a benzyloxycarbonyl group, and a benzyl group.

(26) A method as set forth in (20) or (21) above, wherein the reaction of an optically active 4-protected hydroxypyroglutamic acid compound represented by formula (8) with N-protected-3-halogenomethylindole represented by formula (5) is performed in the presence of a base.

(27) A method as set forth in (26) above, wherein the base is one or more kinds of base selected from the group consisting of a lithium salt of hexamethyldisilazane, lithium hexamethyldisilazane, a potassium salt of hexamethyldisilazane, potassium hexamethyl-disilazane, a sodium salt of hexamethyldisilazane, sodium hexamethyldisilazane, lithium diisopropylamide, and normal butyl lithium.

(28) A method as set forth in (26) above, wherein the base is used in a molar ratio of between 1.0 and 2.0 to 1 relative to the 4-protected hydroxyglutamic acid compound.

(29) A method of manufacturing a (2R, 4R)-monatin compound represented by formula (13) below (including one in the form of a salt), comprising:

(a) reacting a (2R)-4-protected hydroxy-pyroglutamic acid compound represented by formula (11) below (including one in the form of a salt) with N-protected-3-halogenomethylindole represented by formula (15) below to obtain a (2R, 4R)-4-protected hydroxy-4-substituted pyroglutamic acid compound represented by formula (12) below (including one in the form of a salt); and (b) subjecting the (2R, 4R)-4-protected hydroxy-4-substituted pyroglutamic acid compound represented by formula (12) to hydrolysis and deprotection:

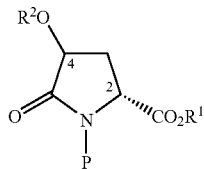

(11)

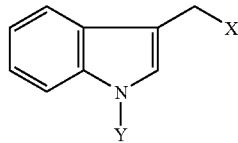

(5)

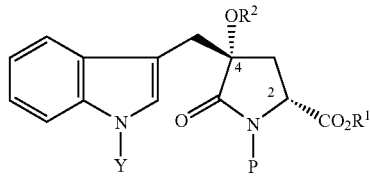

(12)

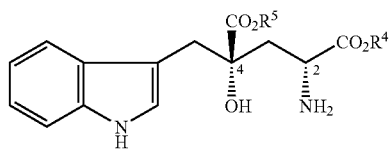

(13)

where $R^1$, $R^4$ and $R^5$ each independently of one another represent a group selected from a hydrogen atom and a hydrocarbon group, $R^2$ represents a protecting group for a hydroxyl group, X represents a halogen atom, P represents a protecting group for an imino group, Y represents a protecting group for an indolyl group, and the configuration at the 4-position in formula (11) is R, S or RS.

(30) A method of manufacturing a (2R, 4R)-4-protected hydroxy-4-substituted pyroglutamic acid compound represented by formula (12) below (including one in the form of a salt), comprising:

(a) reacting a (2R)-4-protected hydroxypyroglutamic acid compound represented by formula (11) below (including one in the form of a salt) with N-protected-3-halogenomethylindole represented by formula (5) below:

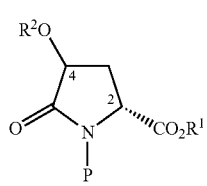

(11)

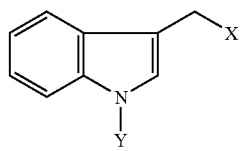

(5)

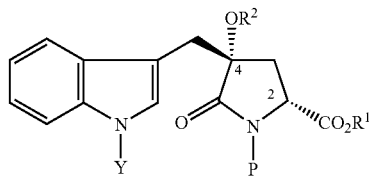

(12)

where $R^1$ represents a group selected from a hydrogen atom and a hydrocarbon group, $R^2$ represents a protecting group for a hydroxyl group, X represents a halogen atom, P represents a protecting group for an imino group, Y represents a protecting group for an indolyl group, and the configuration at the 4-position in formula (11) is R, S or RS.

(31) A method of manufacturing a (2R, 4R)-monatin compound represented by formula (13) below (including one in the form of a salt), comprising:

(a) subjecting a (2R, 4R)-4-protected hydroxy-4-substituted pyroglutamic acid compound represented by formula (12) below (including one in the form of a salt) to hydrolysis and deprotection:

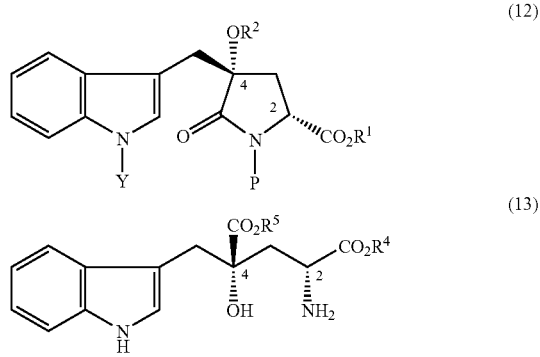

where $R^1$, $R^4$ and $R^5$ each independently of one another represent a group selected from a hydrogen atom and a hydrocarbon group, $R^2$ represents a protecting group for a hydroxyl group, P represents a protecting group for an imino group, Y represents a protecting group for an indolyl group.

(32) A method as set forth in (29) above, wherein $R^1$ represents a group selected from an alkyl group having 1 to 5 carbon atoms and a benzyl group, $R^4$ and $R^5$ each represent a hydrogen atom, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, X represents a group selected from the group consisting of a chlorine atom, a bromine atom, and an iodine atom, and P and Y each independently of each other represent a group selected from the group consisting of a t-butoxycarbonyl group, a benzyloxycarbonyl group, and a benzyl group.

(33) A method as set forth in (30) above, wherein $R^1$ represents a group selected from the group consisting of a hydrogen atom, an alkyl group having 1 to 5 carbon atoms, and a benzyl group, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, X represents a group selected from the group consisting of a chlorine atom, a bromine atom, and an iodine atom, and P and Y each independently of each other represent a group selected from the group consisting of a t-butoxycarbonyl group, a benzyloxycarbonyl group, and a benzyl group.

(34) A method as set forth in (31) above, wherein $R^1$ represents a group selected from an alkyl group having 1 to 5 carbon atoms and a benzyl group, $R^4$ and $R^5$ each represent for a hydrogen atom, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, and P and Y each independently of each other represent a group selected from the group consisting of a t-butoxycarbonyl group, a benzyloxycarbonyl group, and a benzyl group.

(35) A method as set forth in (29) or (30) above, wherein the reaction of a (2R)-4-protected hydroxypyroglutamic acid compound represented by formula (11) with N-protected-3-halogenomethylindole represented by formula (5) is performed in the presence of a base.

(36) A method as set forth in (26) above, wherein the base is one or more kinds of base selected from the group consisting of a lithium salt of hexamethyldisilazane, lithium hexamethyldisilazane, a potassium salt of hexamethyldisilazane, potassium hexamethyl-disilazane, a sodium salt of hexamethyldisilazane, sodium hexamethyldisilazane, lithium diisopropylamide, and normal butyl lithium.

(37) A method as set forth in (26) above, wherein the base is used in a molar ratio of between 1.0 and 2.0 to 1 relative to the 4-protected hydroxyglutamic acid compound.

(38) A method as set forth in (29) above, wherein $R^1$ represents a methyl group, $R^4$ and $R^5$ each represent a hydrogen atom, $R^2$ represents a t-butyldimethylsilyl group, X represents a bromine atom, and P and Y each represent a t-butoxycarbonyl group.

(39) A method as set forth in (30) above, wherein $R^1$ represents a methyl group, $R^2$ represents a t-butyldimethylsilyl group, X represents a bromine atom, and P and Y each represent a t-butoxycarbonyl group.

(40) A method as set forth in (31) above, wherein $R^1$ represents a methyl group, $R^4$ and $R^5$ each represent a hydrogen atom, $R^2$ represents a t-butyldimethylsilyl group, and P and Y each represent a t-butoxycarbonyl group.

(41) A (2R)-4-hydroxypyroglutamic acid compound represented by formula (11) below (including one in the form of a salt):

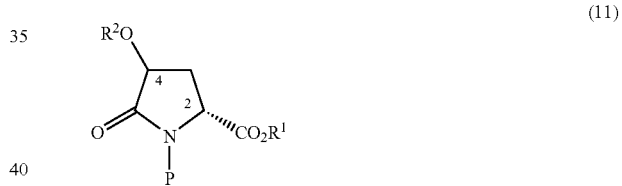

where $R^1$ represents a group selected from a hydrogen atom and a hydrocarbon group, $R^2$ represents a protecting group for a hydroxyl group, P represents a protecting group for an imino group, and the configuration at the 4-position in formula (11) is R, S or RS.

(42) A (2R)-4-hydroxypyroglutamic acid compound as set forth in (41) above, wherein $R^1$ represents a group selected from an alkyl group having 1 to 5 carbon atoms and a benzyl group, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, and P represents a group selected from the group consisting of a t-butoxycarbonyl group, a benzyloxycarbonyl group, and a benzyl group.

(43) A (2R)-4-hydroxypyroglutamic acid compound as set forth in (41) above, wherein $R^1$ represents a methyl group, $R^2$ represents a t-butyldimethylsilyl group, and P represents a t-butoxycarbonyl group.

(44) An N-t-butoxycarbonyl-4-t-butyldimethylsilyloxy-D-pyroglutamic acid methyl ester represented by formula (14) below:

(14)

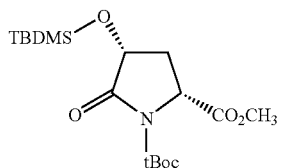

where tBoc represents a t-butoxycarbonyl group and TBDMS represents a t-butyldimethylsilyloxy group.

45) A 4-protected hydroxyl-4-substituted pyroglutamic acid compound represented by formula (2) (including one in the form of a salt):

(2)

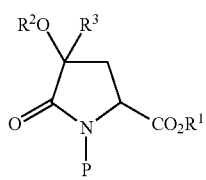

where $R^1$ represents a group selected from a hydrogen atom and a hydrocarbon group, $R^2$ represents a protecting group for a hydroxyl group, $R^3$ represents a group selected from a hydrocarbon group optionally having a substituent and a heterocyclyl hydrocarbon group, and P represents a protecting group for an imino group.

(46) A 4-protected hydroxyl-4-substituted pyroglutamic acid compound as set forth in (45) above, wherein $R^1$ represents a group selected from an alkyl group having 1 to 5 carbon atoms and a benzyl group, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, $R^3$ represents a group selected from the group consisting of an alkyl group having 1 to 20 carbon atoms, an aryl group having 1 to 20 carbon atoms, an aralkyl group having 1 to 20 carbon atoms, and a heterocyclyl hydrocarbon group having 1 to 20 carbon atoms, and P represents a group selected from the group consisting of a t-butoxycarbonyl group, a benzyloxycarbonyl group, and a benzyl group.

(47) A 4-protected hydroxy-4-substituted pyroglutamic acid compound represented by formula (6) (including one in the form of a salt):

(6)

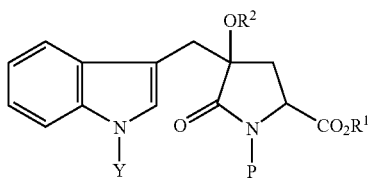

where $R^1$ represents a group selected from a hydrogen atom and a hydrocarbon group, $R^2$ represents a protecting group for a hydroxyl group, P represents a protecting group for an imino group, and Y represents a protecting group for an indolyl group.

(48) A 4-protected hydroxyl-4-substituted pyroglutamic acid compound as set forth in (47) above, wherein $R^1$ represents a group selected from an alkyl group having 1 to 5 carbon atoms and a benzyl group, $R^2$ represents a group selected from a t-butyldimethylsilyl group, a trimethylsilyl group, a t-butyldiphenylsilyl group, a benzyl group, a t-butyl group, a benzyloxycarbonyl group, and a t-butoxycarbonyl group, and P represents a group selected from a t-butoxycarbonyl group, a benzyloxycarbonyl group, and a benzyl group.

(49) A (2R, 4R)-4-protected hydroxy-4-substituted pyroglutamic acid compound represented by formula (12) (including one in the form of a salt):

(12)

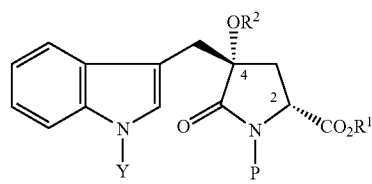

where $R^1$ represents a group selected from a hydrogen atom and a hydrocarbon group, $R^2$ represents a protecting group for a hydroxyl group, P represents a protecting group for an imino group, and Y represents a protecting group for an indolyl group.

(50) A (2R, 4R)-4-protected hydroxy-4-substituted pyroglutamic acid compound as set forth in (49) above, wherein $R^1$ represents a group selected from an alkyl group having 1 to 5 carbon atoms and a benzyl group, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, and P and Y each independently of each other represent a group selected from the group consisting of a t-butoxycarbonyl group, a benzyloxycarbonyl group, and a benzyl group.

(51) An N-t-butoxycarbonyl-(4R)-4-t-butyldimethylsilyloxy-4-benzyl-D-pyroglutamic acid methyl ester represented by formula (15) below:

(15)

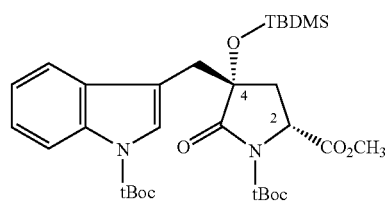

where tBoc represents a t-butoxycarbonyl group and TBDMS represents a t-butyldimethylsilyloxy group.

DETAILED DESCRIPTION OF THE PREFERRED EMBODIMENTS

While it is known that naturally occurring monatin presents the (2S, 4S) form in its stereostructure, the term "monatin" as herein used covers all the compounds having the same structural formula, but differing in configuration, as well as racemic mixtures and mixtures containing any degree of enantiomeric excess of any one or more enantiomers. The individual stereoisomers may be called by designations indicating their stereoisomerism like "(2S, 4S)-monatin" and "(2R, 4R)-monatin."

According to the present invention, a glutamic acid derivative represented by formula (3) is manufactured by subjecting a 4-protected hydroxy-pyroglutamic acid derivative represented by formula (1) to an alkylation reaction to prepare a 4-protected hydroxy-4-substituted pyroglutamic acid derivative represented by formula (2) and subjecting the 4-protected hydroxy-4-substituted pyroglutamic acid derivative to hydrolysis and deprotection steps.

The compounds represented by formulas (1), (2), and (3) may each be in the form of a salt. Any reference made herein to any of those compounds covers its salts unless otherwise noted. For example, in the event that at least one of $R^1$, $R^4$, and $R^5$ is a hydrogen atom, i.e., in the event that the compound has a carboxyl group, the 4-protected hydroxypyroglutamic acid derivative as represented by formula (1), the 4-protected hydroxyl-4-substituted pyroglutamic acid derivative as represented by formula (2), and the 4-protected hydroxyl-4-substituted glutamic acid derivative (glutamic acid derivative) as represented by formula (3) may be in the form of their salts. The salt may, for example, be a salt formed by reacting any such compound with a base, such as sodium hydroxide, potassium hydroxide, or ammonia, or a salt formed by adding thereto an inorganic acid, such as hydrochloric acid, or an organic acid, such as acetic acid.

In formulas (1) to (3), $R^1$, $R^4$, and $R^5$ stand, each independently of one another, for a group selected from a hydrogen atom and a hydrocarbon group. A group selected from an alkyl group having 1 to 5 carbon atoms and a benzyl group is preferably selected as $R^1$. A hydrogen atom is preferably selected as $R^4$ and $R^5$.

In formulas (1) and (2), $R^2$ stands for a protecting group for a hydroxyl group. Groups which are usually employed in the art may be used as protecting groups for hydroxyl groups, and are, for example, a t-butyldimethylsilyl group, a trimethylsilyl group, a t-butyldiphenylsilyl group, a benzyl group, a t-butyl group, a benzyloxycarbonyl group, and a t-butoxycarbonyl group.

In formulas (1) and (2), P stands for a protecting group for an imino group. Groups which are usually employed in the art as protecting groups for amino and imino groups may be used as protecting groups for imino groups, and are, for example, a t-butoxycarbonyl group, a benzyloxycarbonyl group, and a benzyl group.

In formulas (2) and (3), $R^3$ stands for a group selected from a hydrocarbon group optionally having a substituent and a heterocyclyl hydrocarbon group (i.e., a hydrocarbon group substituted with a heterocyclyl group) optionally having a substituent.

The hydrocarbon group may, for example, be a hydrocarbon group having 1 to 20 carbon atoms and is preferably an alkyl group having 1 to 20 carbon atoms, an aryl group having 1 to 20 carbon atoms, an aralkyl group having 1 to 20 carbon atoms or a heterocyclyl hydrocarbon group having 1 to 20 carbon atoms. The heterocyclyl hydrocarbon group may, for example, be a heterocyclyl hydrocarbon group having 1 to 20 carbon atoms. The hydrocarbon group (or heterocyclyl hydrocarbon group) may have any of a chain structure, a cyclic structure, or both. In the event that it has a chain structure, it may be a straight or branched chain.

The substituent which it may optionally have may, for example, be a halogen atom (an iodine, bromine, chlorine, or fluorine atom, etc.), a hydroxyl group, an alkyl group having 1 to 3 carbon atoms, an alkoxy group having 1 to 3 carbon atoms or an amino group. In the event that the group represented by $R^3$ has a substituent, such as an amino, imino or hydroxyl group, the substituent may be protected by a protecting group for an amino, imino or hydroxyl group, etc. as mentioned above. In the event that the group represented by $R^3$ has an indolyl group in its skeleton as an indolylmethyl group does, the indolyl group may be protected by a protecting group for an imino group as mentioned above.

Preferred groups represented by $R^3$ are, for example, a benzyl group and an N-protected-3-indolylmethyl group.

In the event that an N-protected-3-indolylmethyl group is used as $R^3$, this invention is suitable for use as a method of manufacturing monatin. The protecting group for an imino group as mentioned above can be mentioned as a protecting group for the indolyl group in the N-protected-3-indolylmethyl group.

The 4-protected hydroxypyroglutamic acid derivative used according to this invention and represented by formula (1) can be prepared easily from 4-hydroxyproline by using the same method as described by X. Zhang et al (see, *Tetrahedron Letters*, vol. 42, pp. 5335-5338 (2001)), or a method similar thereto, or a method for synthesis used commonly in peptide chemistry if required. The intended 4-protected hydroxypyroglutamic acid derivative can be obtained, for example, by introducing a protecting group (for example, a t-butoxycarbonyl group) into the imino group in 4-hydroxyproline and a protecting group (for example, a t-butyldimethylsilyl group) into its hydroxyl group preferably after its esterification (for example, methyl esterification), and subjecting it to an oxidizing reaction with ruthenium oxide and sodium periodate.

As 4-hydroxyproline, it is possible to use each of its optical isomers, i.e. cis-4-hydroxy-L-proline, trans-4-hydroxy-L-proline, cis-4-hydroxy-D-proline, and trans-4-hydroxy-D-proline, depending on the intended compound. For the manufacture of (2S, 4S)-monatin, for example, cis- or trans-4-hydroxy-L-proline is used to prepare a (2S)-4-hydroxypyroglutamic acid derivative as the starting material for the manufacturing method of this invention, and for the manufacture of (2R, 4R)-monatin, cis- or trans-4-hydroxy-D-proline is used to prepare a (2R)-4-hydroxypyroglutamic acid derivative as the starting material for the manufacturing method of this invention.

As the 4-protected hydroxypyroglutamic acid derivative represented by formula (1), it is possible to mention as a preferred example a compound having a methyl group as $R^1$, a t-butyldimethylsilyl group as $R^2$, and a t-butoxycarbonyl group as P. As the 4-protected hydroxyl-4-substituted pyroglutamic acid derivative represented by formula (2), it is possible to mention as a preferred example a compound having a methyl group as $R^1$, a t-butyldimethylsilyl group as $R^2$, an N-t-butoxycarbonyl-3-indolylmethyl group as $R^3$, and a t-butoxycarbonyl group as P.

The (2R)-4-protected hydroxypyroglutamic acid derivative represented by formula (11) in which the stereochemistry at the 2-position is (R) (including one in the form of a salt) is a novel substance.

The alkylation reaction of the 4-protected hydroxypyroglutamic acid derivative represented by formula (1) can be performed in the presence of an alkylating agent. In the context of this invention, "alkylation" does not mean the introduction of an alkyl group alone in the narrow sense of the word, such as a methyl, ethyl or butyl group, but includes, for example, the introduction of a residual hydrocarbon group optionally having a substituent, and more specifically, means the introduction of a group represented by $R^3$ into the 4-protected hydroxypyroglutamic acid derivative represented by formula (1). The term "alkylating agent" means a reagent used in the alkylation. As the alkylating agent, it is possible to mention an alkyl halide (alkyl chloride, alkyl bromide, alkyl iodide, etc.), and more specifically, a compound represented by formula (4) below:

$$R^3—X \qquad (4)$$

(where $R^3$ stands for a group selected from a hydrocarbon group optionally having a substituent and a heterocyclyl hydrocarbon group optionally having a substituent and X stands for a halogen atom.)

A more detailed description has been made of $R^3$ before. As a preferred halogen atom represented by X, it is possible to mention a chlorine, bromine, or iodine atom.

For the manufacture of monatin according to this invention, it is possible to use an N-protected-3-halogeno-methylindole represented by formula (5) below as the alkylating agent:

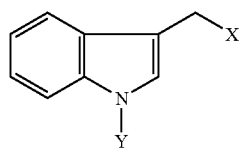

(5)

where Y stands for a protecting group for an indolyl group and X stands for a halogen atom.

Groups which are usually employed in the art as protecting groups for amino and imino groups may be used as protecting groups for indolyl groups represented by Y, and are, for example, a t-butoxycarbonyl group, a benzyloxycarbonyl group, and a benzyl group. The halogen atom represented by X is as mentioned above. N-t-butoxycarbonyl-3-bromomethylindole having a t-butoxycarbonyl group as Y and a bromine atom as X is preferred as the N-protected-3-halogenomethylindole represented by formula (5).

It is preferable to use a base in the alkylation reaction according to this invention. In the event that any base is used, it is possible to mention as examples a lithium salt of hexamethyldisilazane (lithium hexamethyldisilazanide), a potassium salt of hexamethyldisilazane (potassium hexamethyldisilazanide), a sodium salt of hexamethyldisilazane (sodium hexamethyldisilazanide), lithium diisopropylamide, and n-butyl lithium.

The amount of the base to be used can be selected in a molar ratio of preferably, say, between 1.0 and 2.0 and more preferably, say, between 1.0 and 1.3 to 1 of the 4-protected hydroxypyroglutamic acid derivative as the starting substance. In the event that the starting substance is in the form of its salt or contains its salt, the molar ratio can be appropriately selected from the range stated above by considering the molar amount of the 4-protected hydroxypyroglutamic acid derivative in its free form.

The alkylation reaction according to this invention is preferably performed in the presence of a solvent. Any solvent can be used without any particular limitation if it is inert in the reaction. It is possible to mention tetrahydrofuran, ether, dimethoxyethane, toluene, and any mixture thereof as preferred solvents.

In the alkylation reaction according to this invention, it is possible to add HMPA (hexamethylphosphoramide) or DMPU (1,3-dimethyl-3,4,5,6-tetrahydro-2(1H)-pyrimidinone).

In the alkylation reaction according to this invention, it is desirable to use any solvent or additive after removing water therefrom as much as possible in order to have the reaction promoted. It is also desirable to have it performed in an atmosphere of an inert gas, such as nitrogen or argon.

While the reaction time for the alkylation reaction according to this invention is not specifically limited, it is possible to select preferably, say, about 0.5 to 24 hours and more preferably, say, about 1 to 5 hours. While the reaction temperature is not specifically limited, either, it is possible to select preferably, say, about −80° C. to 50° C. and more preferably about −78° C. to 30° C.

After the reaction is over, it is possible to apply appropriate methods known in the art, such as extraction, chromatography, and crystallization, to isolate and refine the intended object. The 4-protected hydroxyl-4-substituted pyroglutamic acid derivative represented by formula (2) is a novel substance.

The 4-protected hydroxyl-4-substituted pyroglutamic acid derivative represented by formula (2) and obtained as described can be led through hydrolysis and deprotection steps to form the glutamic acid derivative represented by formula (3).

The term "hydrolysis and deprotection steps" in the context of this invention means more specifically the steps of performing a hydrolysis reaction and a deprotection reaction for the protecting groups to thereby convert the 4-protected hydroxy-4-substituted pyroglutamic acid derivative represented by formula (2) to the glutamic acid derivative represented by formula (3).

The hydrolysis in the hydrolysis and deprotection steps is defined principally as a reaction for decomposing the bond forming a lactam ring. The deprotection in the hydrolysis and deprotection steps is defined principally as a reaction for removing the protecting group for the hydroxyl group as represented by $R^2$ and the protecting group for the imino group as represented by P.

There is no particular limitation in the order of the hydrolysis and deprotection reactions. It is likely that hydrolysis may also serve as a deprotection reaction (or that the deprotection reaction may also serve as a hydrolysis reaction), and the "hydrolysis and deprotection steps" according to this invention includes such cases where the hydrolysis and deprotection reactions cannot be distinguished clearly from each other.

The ring-opening reaction of the lactam ring by hydrolysis usually produces a carboxyl group at the 4-position having a hydrogen atom as $R^5$ in formula (3), but the carboxyl group at the 4-position may form an ester with alcohol in the event, for example, that hydrolysis is performed in the presence of an alcoholic solvent. In the event that such an ester is not converted to a carboxyl group by hydrolysis and deprotection steps, $R^5$ in formula (3) will be an alcohol-derived hydrocarbon group.

When $R^1$ in formula (2) is a hydrocarbon group, i.e., when —COOR$^1$ is an alkoxycarbonyl group, the alkoxycarbonyl group may be converted to a carboxyl group after the hydrolysis and deprotection steps. In such a case, $R^4$ in formula (3) will be a hydrogen atom even when $R^1$ in formula (2) is a hydrocarbon group. It is possible to include the step of converting the alkoxycarbonyl group to a carboxyl group before the hydrolysis and deprotection steps. When —COOR$^1$ is a benzyloxycarbonyl group ($R^1$ is a benzyl group), for example, it can be converted to a carboxyl group ($R^1$ is a hydrogen atom) by a catalytic hydrogenation reaction prior to the hydrolysis and deprotection steps.

A compound having a hydrocarbon group as $R^2$ and/or $R^3$ in formula (3), i.e., a compound having an alkoxycarbonyl group in formula (3) can be converted to a compound having a hydrogen atom as $R^2$ and/or $R^3$ by having its alkoxycarbonyl group converted to a carboxyl group by a method known in the art, such as hydrolysis with an acid or base.

When the group represented by $R^3$ in formula (2) has a protected imino group, a protected amino group, a protected indolyl group, a protected hydroxyl group, etc. in its structure, it is likely that the protecting group for any such imino, amino, indolyl or hydroxyl group, etc. may undergo deprotection through the hydrolysis and deprotection steps. It is, therefore, likely that $R^3$ in formula (3) and $R^2$ in formula (2) may not represent the same group.

The hydrolysis reaction can be performed by a reaction with a base, a reaction with an acid, a catalytic hydrogenation reaction, a reaction with a fluoride, etc. The deprotection reaction can also be performed by any such reaction.

A hydrolysis reaction with a base is preferably employed for the hydrolysis reaction of the lactam ring. It is preferable to use lithium hydroxide, sodium hydroxide, potassium hydroxide, etc. as the base.

When a base is used, its amount can be selected in a molar ratio of preferably, say, about 1 to 50 and more preferably, say, about 5 to 20 of base to 1 mole of the compound (in its free form). In the event that the 4-protected hydroxy-4-substituted pyro-glutamic acid derivative is in the form of its salt or contains its salt, the molar ratio can be appropriately selected from the range stated above by considering the molar amount of the 4-protected hydroxy-4-substituted pyroglutamic acid derivative in its free form.

As the solvent to be used in the hydrolysis reaction, it is possible to use a mixed solvent of water and an organic solvent miscible with water, as a reaction solvent, such as methanol, ethanol, isopropanol or other alcohol, tetrahydrofuran or acetonitrile.

The hydrolysis reaction usually causes the hydrolysis of the ester bond, as well as the lactam ring, and converts the alkoxycarbonyl group existing in the compound to a carboxyl group.

The reaction time for hydrolysis may be selected from preferably, say, about 1 to 48 hours and more preferably, say, about 3 to 15 hours. The reaction temperature for hydrolysis may be selected from preferably, say, about 0° C. to 100° C. and more preferably, say, about 20° C. to 50° C.

Any method of deprotection that is usually employed in peptide chemistry, etc. may be followed for the deprotection of the protecting groups in the 4-protected hydroxy-4-substituted pyroglutamic acid derivative represented by formula (2), for example, for the removal of the protecting groups for the imino group, amino group, indolyl group, hydroxyl group, etc. For example, it can be performed in the same way with the hydrolysis reaction as described above. For example, the t-butoxycarbonyl and t-butyldimethylsilyl groups can be removed with an acid, and the benzyloxycarbonyl group by a catalytic hydrogenation reaction. A fluoride can be used for the deprotection of only the t-butyldimethylsilyl group, for example.

After the reaction is over, it is possible to apply appropriate methods known in the art, such as extraction, chromatography and crystallization, to isolate and refine the glutamic acid derivative manufactured by the method of the present invention and represented by formula (3). It is preferably obtained as crystals by crystallizing the product from water, alcohol or a mixed solvent thereof in the form of its salt with an acid, such as hydrochloric acid, its salt with a base, such as ammonia, or its salt with a metal, such as sodium, or in its free form.

When the glutamic acid derivative has been obtained in the form of a salt, it is possible to convert its salt to its free form or change it to another salt, or when it has been obtained in its free form, it is possible to convert it to a salt, by employing any appropriate reaction known in the art, such as a free body forming reaction, a reaction for forming another salt or a salt changing reaction.

The alkylation reaction in the method of the present invention makes it possible to have an intended group react selectively with the 4-position of the 4-protected hydroxypyroglutamic acid derivative represented by formula (1) and this reaction proceeds stereoselectively. The configuration is retained until after the hydrolysis and deprotection steps. Accordingly, the method of the present invention is very useful as a method of manufacturing 4-protected hydroxyl-4-substituted pyroglutamic acid derivatives having optical activity, glutamic acid derivatives having optical activity, and particularly optically active monatin.

For example, the use of a (2S)-4-protected hydroxyl pyroglutamic acid derivative as the 4-protected hydroxyl pyroglutamic acid derivative represented by formula (1) permits the selective manufacture of (2S, 4S)-monatin represented by formula (19) below and the use of a (2R)-4-protected hydroxyl pyroglutamic acid derivative permits the selective manufacture of (2R, 4R)-monatin represented by formula (20) below:

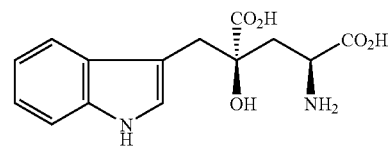

(19)

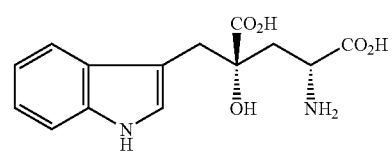

(20)

Other features of the invention will become apparent in the course of the following descriptions of exemplary embodiments which are given for illustration of the invention and are not intended to be limiting thereof.

Examples $^1$H-NMR spectra were determined with a Bruker AVANCE400 (400 MHz), and MS spectra were determined with a Thermo Quest TSQ700.

Example 1

Synthesis of N-t-butoxycarbonyl-4-t-butyldimethylsilyloxy-D-pyroglutamic acid methyl ester

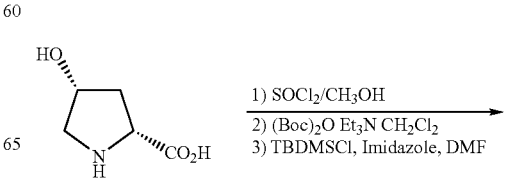

-continued

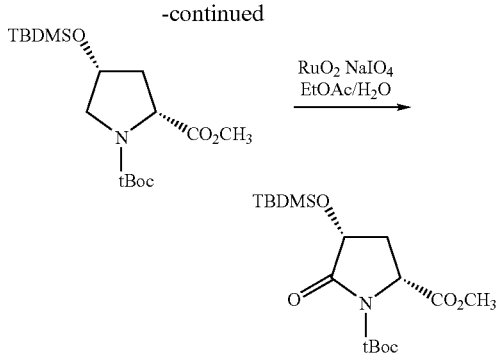

N-t-butoxycarbonyl-4-t-butyldimethylsilyloxy-D-pyroglutamic acid methyl ester was obtained as a colorless oily substance at a total yield of 66% from cis-4-hydroxy-D-proline as a starting material in accordance with the method of X. Zhang et al (see, Tetrahedron Letters, vol. 42, pp. 5335-5338 (2001)).
(MS spectrum)
ESI-MS: 374.6 (M+H)$^+$, 396.59 (M+Na)$^+$.
(NMR spectrum)
$^1$H-NMR (CDCl$_3$, 400 MHz) δ ppm: 0.11 (s, 3H), 0.16 (s, 3H), 0.89 (s, 9H), 1.50 (s, 9H), 1.99 (m, 1H), 2.57 (m, 1H), 3.76 (s, 3H), 4.28 (t, 1H), 4.46 (t, 1H).

Example 2

Synthesis of (2R, 4R)-monatin

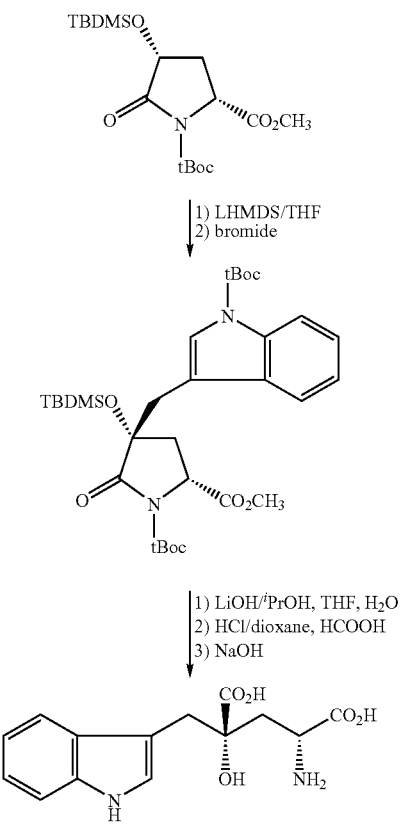

1.45 g (3.9 mmol) of the above N-t-butoxycarbonyl-4-t-butyldimethylsilyloxy-D-pyro-glutamic acid methyl ester were dissolved in 15 ml of anhydrous THF (tetrahydrofuran) in an atmosphere of argon gas. The resulting solution was cooled to −78° C., 2.8 ml (4.8 mmol; 1.7 mM/ml) of LHMDS (lithium hexamethyldisilazane) were added to it, and the mixture was stirred for an hour. A solution obtained by dissolving 1.30 g (4.2 mmol) of N-t-butoxycarbonyl-3-bromomethylindole in 4 ml of THF was added dropwise into the reacted solution and it was stirred at −78° C. for 25 minutes and then at room temperature for two hours. An aqueous solution of ammonium chloride was added to the reacted solution, and extraction was performed twice with 50 ml of ethyl acetate. The organic layer was washed with 50 ml of water and 50 ml of a saturated saline solution and was dried with anhydrous magnesium sulfate. The magnesium sulfate was removed by filtration, and the filtrate was concentrated under reduced pressure. The residue was refined by PTLC (preparative thin-layer chromatography) to yield 1.21 g (2.01 mmol) of N-t-butoxycarbonyl-(4R)-4-t-butyldimethylsilyloxy-4-(N-t-butoxycarbonyl-3-indolylmethyl)-D-pyroglutamic acid methyl ester. Its $^1$H-NMR spectrum showed a peak marked by a very small amount (several percent) of impurity beside the isomers of the compound.
(MS spectrum)
ESI-MS: 626.0 (M+Na)$^+$.
(NMR spectrum)
$^1$H-NMR (CDCl$_3$, 400 MHz) δ ppm: 0.14 (s, 3H), 0.30 (s, 3H), 0.87 (s, 9H), 1.45 (s, 9H), 1.66 (s, 9H), 2.09 (dd, 1H), 2.42 (dd, 1H), 3.02 (d, 1H), 3.19 (d, 1H), 3.71 (s, 3H), 4.16 (m, 1H), 7.22-7.32 (m, 2H), 7.49 (m, 2H), 8.17 (brd, 1H).

544 mg (0.90 mmol) of the above compound were dissolved in a mixed solvent prepared from 6 ml of isopropanol, 3 ml of THF, and 8 ml of water, and the solution was kept at 0° C. 605 mg (14.43 mmol) of lithium hydroxide monohydrate were added to the reacted solution, and the resulting mixture was stirred at room temperature for five hours. The reacted solution was concentrated under reduced pressure, 15 ml of water were added to the residue, and the solution had its pH adjusted to 3 with a 2N solution of hydrochloric acid. Extraction was performed twice with 50 ml of ethyl acetate, and the organic layer was washed with a saturated saline solution and was then dried with anhydrous magnesium sulfate. The magnesium sulfate was removed by filtration, and the filtrate was concentrated under reduced pressure.

The residue was dissolved in 4 ml of formic acid, and the reacted solution was kept at 0° C. 4 ml of a 4N HCl/dioxane solution were added to it, and the mixture was stirred at room temperature for 30 minutes. The reacted solution was concentrated under reduced pressure, and the residue was dissolved in 10 ml of water and washed with 20 ml of ether and 20 ml of ethyl acetate. The aqueous solution was neutralized with a 2N solution of NaOH, and, after it was concentrated to about one-fifth, 20 ml of ethanol were added to it. The resulting crystals was collected by filtration and dried under reduced pressure to yield 155 mg (0.49 mmol) of (2R, 4R)-monatin as a sodium salt. Its analysis for optical isomers was conducted by HPLC (high performance liquid chromatography) using a chiral column and revealed only the (2R, 4R) and (2R, 4S) forms of isomers having an integrated peak ratio of 98:2.
(MS spectrum)
ESI-MS: 291 (M−H)$^-$.
(NMR spectrum)
$^1$H-NMR (D$_2$O, 400 MHz) δ ppm:
<Sodium salt of (2R, 4R)-monatin>
1.99 (dd, 1H, J=11.8 Hz, J=15.2 Hz), 2.60 (dd, 1H, J=1.9 Hz, J=15.2 Hz), 3.02 (d, 1H, J=14.6 Hz), 3.22 (d, 1H, J=14.6

Hz), 3.57 (d, 1H, J=10.2 Hz), 7.08 (t, 1H, J=7.2 Hz), 7.15 (t, 1H, J=7.2 Hz), 7.16 (s, 1H), 7.42 (d, 1H, J=8.0 Hz), 7.66 (d, 1H, J=8.0 Hz).

Example 3

Synthesis of (2R, 4R)-4-hydroxy-4-benzylglutamic acid

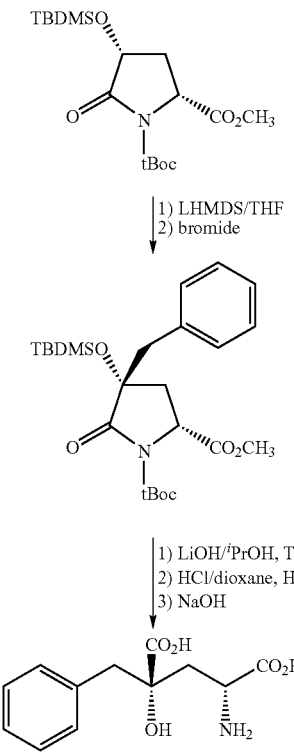

N-t-butoxycarbonyl-(4R)-4-t-butyldimethylsilyloxy-4-benzyl-D-pyroglutamic acid methyl ester was obtained as a solid at a yield of 46.0% by using benzyl bromide instead of N-t-butoxycarbonyl-3-bromomethylindole and otherwise repeating Example 2. Its $^1$H-NMR spectrum showed a single stereoisomer.

(MS spectrum)

ESI-MS: 464.8 (M+H)$^+$, 486.8 (M+Na)$^+$.

(NMR spectrum)

$^1$H-NMR (CDCl$_3$, 400 MHz) δ ppm: 0.13 (s, 3H), 0.29 (s, 3H), 0.86 (s, 9H), 1.46 (s, 9H), 1.96 (dd, 1H), 2.45 (dd, 1H), 2.88 (d, 1H), 3.16 (d, 1H), 3.71 (s, 3H), 3.80 (m, 1H), 7.20-7.31 (m, 5H).

A sodium salt of (2R, 4R)-4-hydroxy-4-benzylglutamic acid was obtained at a yield of 57.4% by using the above compound and otherwise repeating Example 2. Its analysis for optical isomers was conducted by HPLC using a chiral column and revealed only (2R, 4R) and (2R, 4S) forms of isomers having an integrated peak ratio of 99:1 or higher.

(MS spectrum)

ESI-MS: 252 (M−H)$^−$.

(NMR spectrum)

$^1$H-NMR (400 MHz, D$_2$O) δ ppm:

<Sodium salt of (2R, 4R)-4-hydroxy-4-benzylglutamic acid>

1.95 (dd, 1H, J=11.8 Hz, J=15.3 Hz), 2.56 (d, 1H, J=15.2 Hz), 2.81 (d, 1H, J=13.6 Hz), 3.07 (d, 1H, J=13.6 Hz), 3.55 (d, 1H, J=11.8 Hz), 7.19-7.31 (m, 5H).

INDUSTRIAL APPLICABILITY

According to the present invention, it is possible to manufacture efficiently and easily glutamic acid derivatives known to be useful as sweeteners, in particular monatin, and a 4-protected hydroxyl pyroglutamic acid derivative useful as an intermediate in the manufacture thereof. The alkylation reaction of the 4-protected hydroxyl pyroglutamic acid derivative according to the present invention is suitable for use as a method of manufacturing glutamic acid derivatives having optical activity, particularly optically active monatin, since it can be carried out selectively at the 4-position and stereoselectively.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A 4-protected hydroxyl-4-substituted pyroglutamic acid compound represented by formula (2) or a salt thereof:

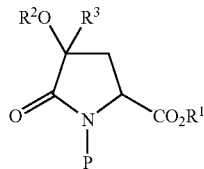

(2)

where $R^1$ represents a group selected from the group consisting of a hydrogen atom and a hydrocarbon group, $R^2$ represents a protecting group for a hydroxyl group, $R^3$ represents a group selected from the group consisting of a hydrocarbon group optionally having a substituent and a heterocyclyl hydrocarbon group, and P represents a protecting group for an imino group.

2. A 4-protected hydroxyl-4-substituted pyroglutamic acid compound as set forth in claim 1, wherein $R^1$ represents a group selected from the group consisting of an alkyl group having 1 to 5 carbon atoms and a benzyl group, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, $R^3$ represents a group selected from the group consisting of an alkyl group having 1 to 20 carbon atoms, an aryl group having 1 to 20 carbon atoms, an aralkyl group having 1 to 20 carbon atoms, and a heterocyclyl hydrocarbon group having 1 to 20 carbon atoms, and P represents a group selected from the group consisting of a t-butoxycarbonyl group, a benzyloxycarbonyl group, and a benzyl group.

3. A 4-protected hydroxy-4-substituted pyroglutamic acid compound represented by formula (6) or a salt thereof:

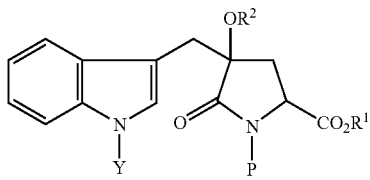
(6)

where $R^1$ represents a group selected from the group consisting of a hydrogen atom and a hydrocarbon group, $R^2$ represents a protecting group for a hydroxyl group, P represents a protecting group for an imino group, and Y represents a protecting group for an indolyl group.

4. A 4-protected hydroxy-4-substituted pyroglutamic acid compound as set forth in claim 3, wherein $R^1$ represents a group selected from the group consisting of an alkyl group having 1 to 5 carbon atoms and a benzyl group, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, and P represents a group selected from the group consisting of a t-butoxycarbonyl group, a benzyloxycarbonyl group, and a benzyl group.

5. A (2R,4R)-4-protected hydroxy-4-substituted pyroglutamic acid compound represented by formula (12) or a salt thereof:

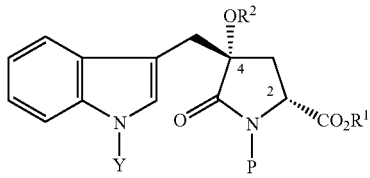
(12)

where $R^1$ represents a group selected from the group consisting of a hydrogen atom and a hydrocarbon group, $R^2$ represents a protecting group for a hydroxyl group, P represents a protecting group for an imino group, and Y represents a protecting group for an indolyl group.

6. A (2R,4R)-4-protected hydroxy-4-substituted pyroglutamic acid compound as set forth in claim 5, wherein $R^1$ represents a group selected from the group consisting of an alkyl group having 1 to 5 carbon atoms and a benzyl group, $R^2$ represents a group selected from the group consisting of a t-butyldimethylsilyl group, a trimethylsilyl group, a t-butyldiphenylsilyl group, a benzyl group, a t-butyl group, a benzyloxycarbonyl group, and a t-butoxycarbonyl group, and P and Y each independently of each other represent a group selected from the group consisting of a t-butoxycarbonyl group, a benzyloxycarbonyl group, and a benzyl group.

7. An N-t-butoxycarbonyl-(4R)-4-t-butyldimethylsilyloxy-4-benzyl-D-pyroglutamic acid methyl ester represented by formula (15) below:

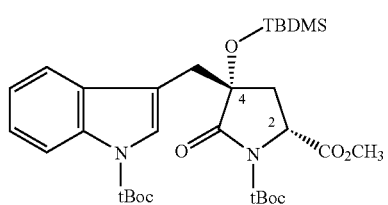
(15)

where tBoc represents a t-butoxycarbonyl group and TBDMS represents a t-butyldimethylsilyl group.

* * * * *